US012303151B2

(12) United States Patent
Quillin

(10) Patent No.: US 12,303,151 B2
(45) Date of Patent: May 20, 2025

(54) ASPIRATION MEDICAL DEVICE

(71) Applicant: BOSTON SCIENTIFIC SCIMED, INC., Maple Grove, MN (US)

(72) Inventor: Daniel T. Quillin, Eden Prairie, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 18/631,786

(22) Filed: Apr. 10, 2024

(65) Prior Publication Data

US 2024/0268841 A1    Aug. 15, 2024

Related U.S. Application Data

(63) Continuation of application No. 17/736,244, filed on May 4, 2022, now Pat. No. 11,969,176.

(60) Provisional application No. 63/183,856, filed on May 4, 2021.

(51) Int. Cl.
*A61B 17/22*    (2006.01)
*A61M 25/00*    (2006.01)

(52) U.S. Cl.
CPC ........... *A61B 17/22* (2013.01); *A61M 25/007* (2013.01); *A61B 2017/22079* (2013.01); *A61B 2017/22084* (2013.01)

(58) Field of Classification Search
CPC .............. A61F 17/22; A61F 17/32037; A61B 2017/22079; A61B 2017/22084; A61B 2090/0801; A61B 2217/005; A61M 25/007

USPC .............................. 606/128; 604/35, 19, 207
See application file for complete search history.

(56) References Cited

U.S. PATENT DOCUMENTS

| | | | |
|---|---|---|---|
| 2,568,566 A | 9/1951 | Sokolik | |
| 5,180,364 A * | 1/1993 | Ginsburg | A61M 25/0075 604/510 |
| 5,312,356 A | 5/1994 | Engelson et al. | |
| 5,425,723 A | 6/1995 | Wang | |

(Continued)

FOREIGN PATENT DOCUMENTS

| EP | 0788774 A1 | 8/1997 |
|---|---|---|
| EP | 1092396 A2 | 4/2001 |

(Continued)

OTHER PUBLICATIONS

International Search Report and Written Opinion dated Jul. 22, 2022 for International Application No. PCT/US2022/027588.

(Continued)

*Primary Examiner* — Jocelin C Tanner
(74) *Attorney, Agent, or Firm* — Seager, Tufte & Wickhem, LLP

(57) ABSTRACT

Aspiration medical devices and methods for making and using aspiration medical devices are disclosed. An example aspiration medical device may include a catheter shaft having a distal end region and defining an inflow orifice adjacent to the distal end region. An aspiration member may be disposed within the catheter shaft. The aspiration member may have a plurality of axially-spaced fluid jets formed therein. A collar may be disposed over the aspiration member. The collar may have a jet support region disposed adjacent to at least one of the fluid jets and a wall support region disposed adjacent to a wall of the catheter shaft.

20 Claims, 15 Drawing Sheets

(56) References Cited

U.S. PATENT DOCUMENTS

| | | |
|---|---|---|
| 5,976,103 A | 11/1999 | Martin |
| 5,989,271 A | 11/1999 | Bonnette et al. |
| 6,569,145 B1 | 5/2003 | Shmulewitz et al. |
| 6,875,193 B1 | 4/2005 | Bonnette et al. |
| 7,226,433 B2 | 6/2007 | Bonnette et al. |
| 8,998,843 B2 | 4/2015 | Bonnette et al. |
| 9,078,691 B2 | 7/2015 | Morris et al. |
| 2004/0073141 A1 | 4/2004 | Hartley et al. |
| 2006/0129091 A1 | 6/2006 | Bonnette et al. |
| 2006/0135870 A1 | 6/2006 | Webler |
| 2006/0138379 A1 | 6/2006 | Jacobsen et al. |
| 2007/0265647 A1 | 11/2007 | Bonnette et al. |
| 2008/0188831 A1 | 8/2008 | Bonnette et al. |
| 2008/0275383 A1 | 11/2008 | Weisel et al. |
| 2011/0015564 A1 | 1/2011 | Bonnette et al. |
| 2014/0155830 A1 | 6/2014 | Bonnette et al. |
| 2014/0228869 A1 | 8/2014 | Bonnette et al. |
| 2014/0277006 A1 | 9/2014 | Bonnette et al. |
| 2014/0343457 A1 | 11/2014 | Shekalim et al. |
| 2017/0252057 A1 | 9/2017 | Bonnette et al. |
| 2018/0235648 A1 | 8/2018 | Wilke et al. |
| 2019/0209745 A1* | 7/2019 | Hanson ............ A61B 17/32037 |
| 2019/0217069 A1 | 7/2019 | Walzman |
| 2020/0113593 A1 | 4/2020 | Behera |
| 2020/0306501 A1 | 10/2020 | Yee et al. |

FOREIGN PATENT DOCUMENTS

| | | |
|---|---|---|
| EP | 2712559 A2 | 4/2014 |
| WO | 9613295 A1 | 5/1996 |
| WO | 2008097993 A2 | 8/2008 |
| WO | 2017152086 A1 | 9/2017 |

OTHER PUBLICATIONS

Invitation to Pay Additional Fees dated Apr. 21, 2017 for International Application No. PCT/US2017/020717.

International Search Report and Written Opinion for Application No. PCT/US2019/018762, 14 pages, dated Apr. 20, 2018.

International Search Report and Written Opinion for Application No. PCT/US2019/013108, 12 pages, dated Apr. 18, 2019.

* cited by examiner

ASPIRATION MEDICAL DEVICE

CROSS REFERENCE TO RELATED APPLICATIONS

This application is a continuation of U.S. patent application Ser. No. 17/736,244, filed May 4, 2022, which claims the benefit of and priority to U.S. Provisional Patent Application Ser. No. 63/183,856 filed on May 4, 2021, the disclosure of which is incorporated herein by reference.

TECHNICAL FIELD

The present disclosure pertains to medical devices, and methods for manufacturing medical devices. More particularly, the present disclosure pertains to aspiration medical devices.

BACKGROUND

A wide variety of medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An aspiration medical device is disclosed. The aspiration medical device comprises: a catheter shaft having a distal end region and defining an inflow orifice adjacent to the distal end region; an aspiration member disposed within the catheter shaft, the aspiration member having a plurality of axially-spaced fluid jets formed therein; and a collar disposed over the aspiration member, the collar having a jet support region disposed adjacent to at least one of the fluid jets and a wall support region disposed adjacent to a wall of the catheter shaft.

Alternatively or additionally to any of the embodiments above, the aspiration member has a closed distal end.

Alternatively or additionally to any of the embodiments above, at least some of the fluid jets are angled proximally.

Alternatively or additionally to any of the embodiments above, at least some of the fluid jets are oriented in a direction that is normal to a longitudinal axis of the aspiration member.

Alternatively or additionally to any of the embodiments above, the jet support region includes a jet opening that is aligned with one of the fluid jets.

Alternatively or additionally to any of the embodiments above, the jet opening is angled proximally.

Alternatively or additionally to any of the embodiments above, the jet support region and the wall support region are coaxially arranged.

Alternatively or additionally to any of the embodiments above, the jet support region is radially offset from a longitudinal axis of the wall support region.

Alternatively or additionally to any of the embodiments above, further comprising a second collar disposed over the aspiration member.

Alternatively or additionally to any of the embodiments above, the second collar includes a second jet support region that is aligned with one of the fluid jets.

Alternatively or additionally to any of the embodiments above, the collar is axially spaced apart from the second collar.

An aspiration medical device is disclosed. The aspiration medical device comprises: a catheter shaft having a distal end region, the catheter shaft including an inflow orifice adjacent to the distal end region and an outflow orifice disposed proximally of the inflow orifice; an aspiration member disposed within the catheter shaft, the aspiration member having a plurality of axially-spaced fluid jets formed therein including a first fluid jet; and a first collar disposed along the aspiration member and positioned adjacent to the first fluid jet, the first collar having a jet support region and a wall support region.

Alternatively or additionally to any of the embodiments above, the first fluid jet is oriented orthogonally to a longitudinal axis of the aspiration member.

Alternatively or additionally to any of the embodiments above, the jet support region includes a first jet opening that is aligned with the first fluid jet.

Alternatively or additionally to any of the embodiments above, the first jet opening is angled proximally.

Alternatively or additionally to any of the embodiments above, the plurality of axially-spaced fluid jets includes a second fluid jet; and further comprising a second collar disposed along the aspiration member and positioned adjacent to the second fluid jet.

Alternatively or additionally to any of the embodiments above, the first collar is co-axially disposed within the catheter shaft.

Alternatively or additionally to any of the embodiments above, the first collar includes a second jet opening.

Alternatively or additionally to any of the embodiments above, the aspiration member includes a second fluid jet disposed opposite the first fluid jet, and wherein the first collar includes a first jet opening aligned with the first fluid jet and a second jet opening aligned with the second fluid jet.

An aspiration medical device is disclosed. The aspiration medical device, comprises: a catheter shaft having a distal end region and an inflow orifice disposed along the distal end region; an aspiration tube disposed within the catheter shaft, the aspiration tube having a closed distal end and having a plurality of axially-spaced fluid jets formed therein; wherein the plurality of axially-spaced fluid jets includes a first fluid jet; and a metallic 3-D printed collar disposed along the aspiration tube and aligned with the first fluid jet, the collar having a jet support region configured to support the first fluid jet and a wall support region configured to support a wall region of the catheter shaft disposed opposite the first fluid jet.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
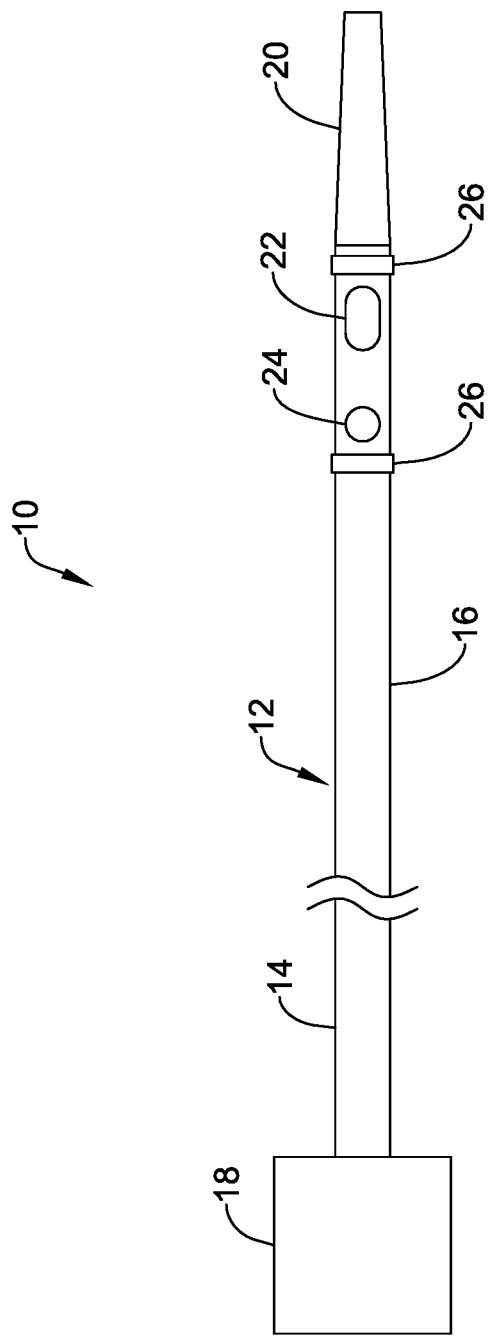
FIG. 1 is a side view of an example aspiration medical device.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

FIG. 1 is a side view of an example aspiration medical device 10. The aspiration medical device 10 may include a tubular member or catheter shaft 12 having a proximal end region 14 and a distal end region 16. A hub or manifold 18 (depicted schematically) may be coupled to the proximal end region 14. A tip member 20 may be coupled to the distal end region 16. The catheter shaft 12 may include a number of additional features. For example, one or more markers 26 (e.g., radiopaque marker bands) may be disposed along the catheter shaft 12.

The catheter shaft 12 may have a plurality of openings or orifices. For example, the catheter shaft 12 may have a first or inflow orifice 22. The inflow orifice 22 may be disposed proximally of the distal end of the catheter shaft. The catheter shaft 12 may also include a second or outflow orifice 24. The outflow orifice 24 may be disposed proximally of the inflow orifice 22. In some instances, the inflow orifice 22 and the outflow orifice 24 may be axially aligned along the catheter shaft 12. In other instances, the inflow orifice 22 and the outflow orifice 24 may be circumferentially offset from one another about the catheter shaft 12. In some instances, the inflow orifice 22 and the outflow orifice 24 may have the same size, shape, or both. In other instances, the inflow orifice 22 and the outflow orifice 24 may differ in size, shape, or both.

Figure 2:
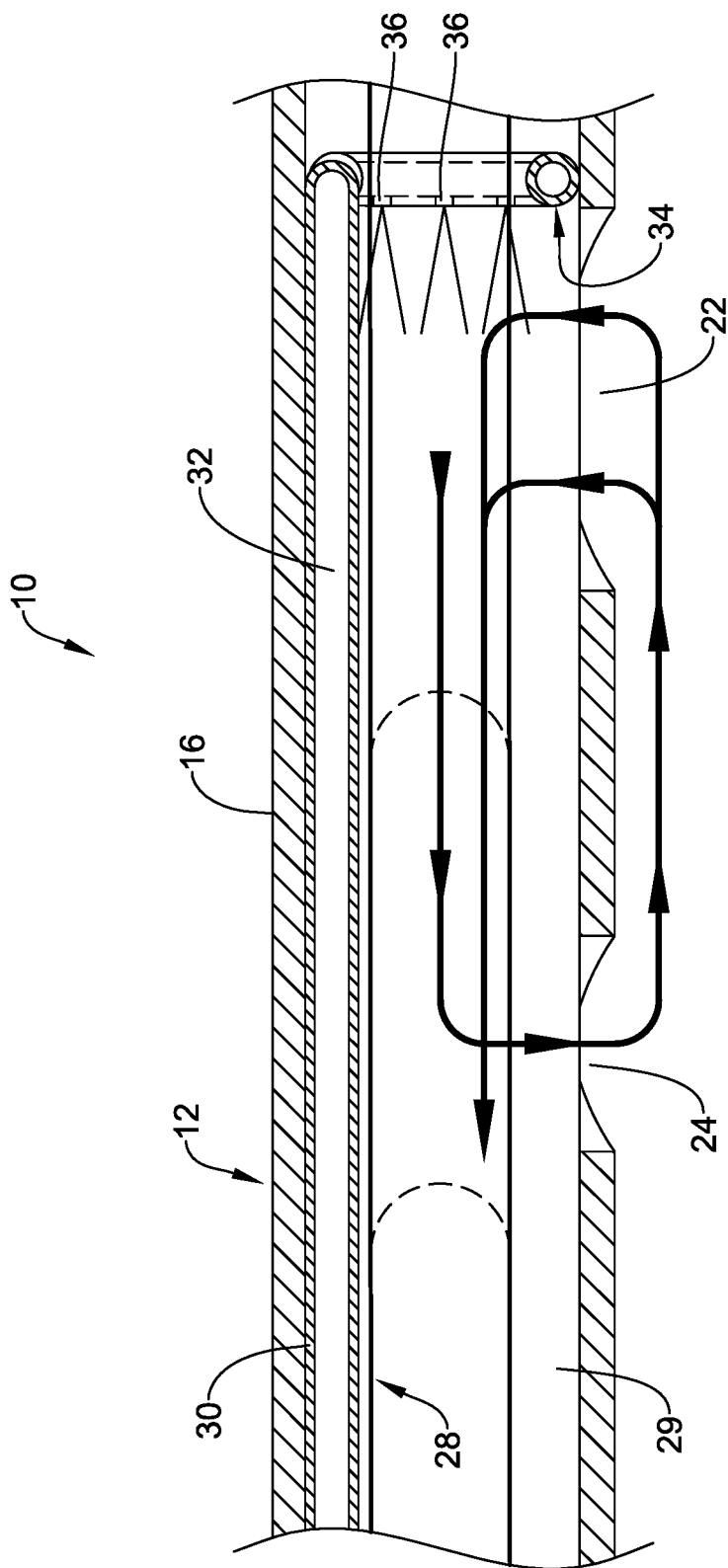
FIG. 2 is a cross-sectional side view of a portion of an example aspiration medical device.

FIG. 2 is a cross-sectional view of a portion of the aspiration medical device 10 that schematically depicts how the aspiration medical device 10 may be used to aspirate material (e.g., embolic material, thrombus/thrombogenic material, stenotic material, etc.) from a patient. Here it can be seen that an aspiration assembly 28 may be disposed within a lumen 29 of the catheter shaft 12. The aspiration assembly 28 may include a tubular member or inner tube 30 defining a lumen 32. A fluid jet 34 may be coupled to the inner tube 30. In some instances, the fluid jet 34 may be understood to be or otherwise take the form of a fluid jet orifice or fluid jet orifice member. The fluid jet 34 may be in fluid communication with the lumen 32. In some instances, the fluid jet 34 may be oriented at an angle relative to the inner tube 30. For example, the fluid jet 34 may be disposed at an angle that is normal to the inner tube 30. In at least some instances, the fluid jet 34 may have an annular arrangement. However, other arrangements and/or configurations are contemplated.

The fluid jet 34 may have one or more jet orifices 36 define therein. In some instances, the fluid jet 34 includes one jet orifice 36. In other instances, the fluid jet 34 may include two, three, four, five, six, seven, eight, or more jet orifices 36. The jet orifices 36 may take the form of openings in the fluid jet 34 that allow fluid infused through the lumen 32 to be jetted in a generally proximal direction within the lumen 29 of the catheter shaft 12 as depicted by lines in FIG. 2 projecting proximally from the jet orifices 36. The jet orifices 36 may be spaced evenly along the fluid jet 34. Alternatively, the jet orifices may be arranged in an uneven manner or distributed along only a portion of the fluid jet 34.

Infusion of a fluid (e.g., a motive fluid, a liquid, a gas or air, steam, a fluid with particles disposed therein, or the like) though the lumen 32 of the inner tube 30 may cause the fluid to be jetted or otherwise exit the jet orifices 36. As the fluid moves proximally through the lumen 29, the fluid may generate an aspiration force that can draw entrainment material into the lumen 29 through the inflow orifice 22. The material drawn into the lumen 29 may be aspirated through the lumen 29 and out from a patient. In addition or in the alternative, some or all of the thrombogenic material drawn into the lumen 29 may exit that catheter shaft 12 through the outflow orifice 24. The material may recirculate and the action of recirculation may help to break up the thrombogenic material in order to ease removal. For example, the material may enter the inflow orifice 22 where it can be aspirated from the patient and/or further recirculated.

Figure 3:
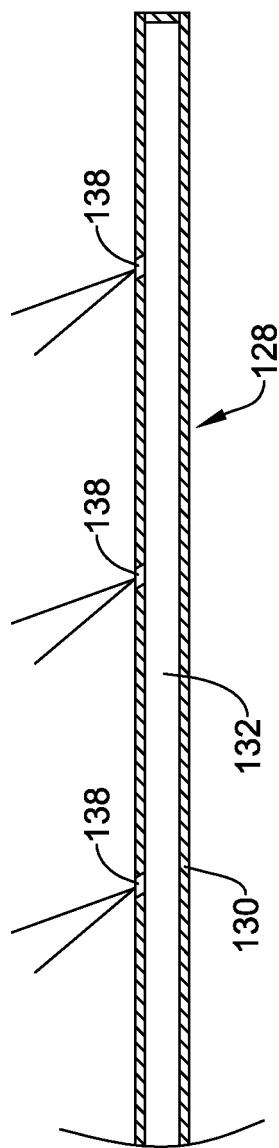
FIG. 3 is a cross-sectional side view of a portion of an example aspiration member.
Figure 4:
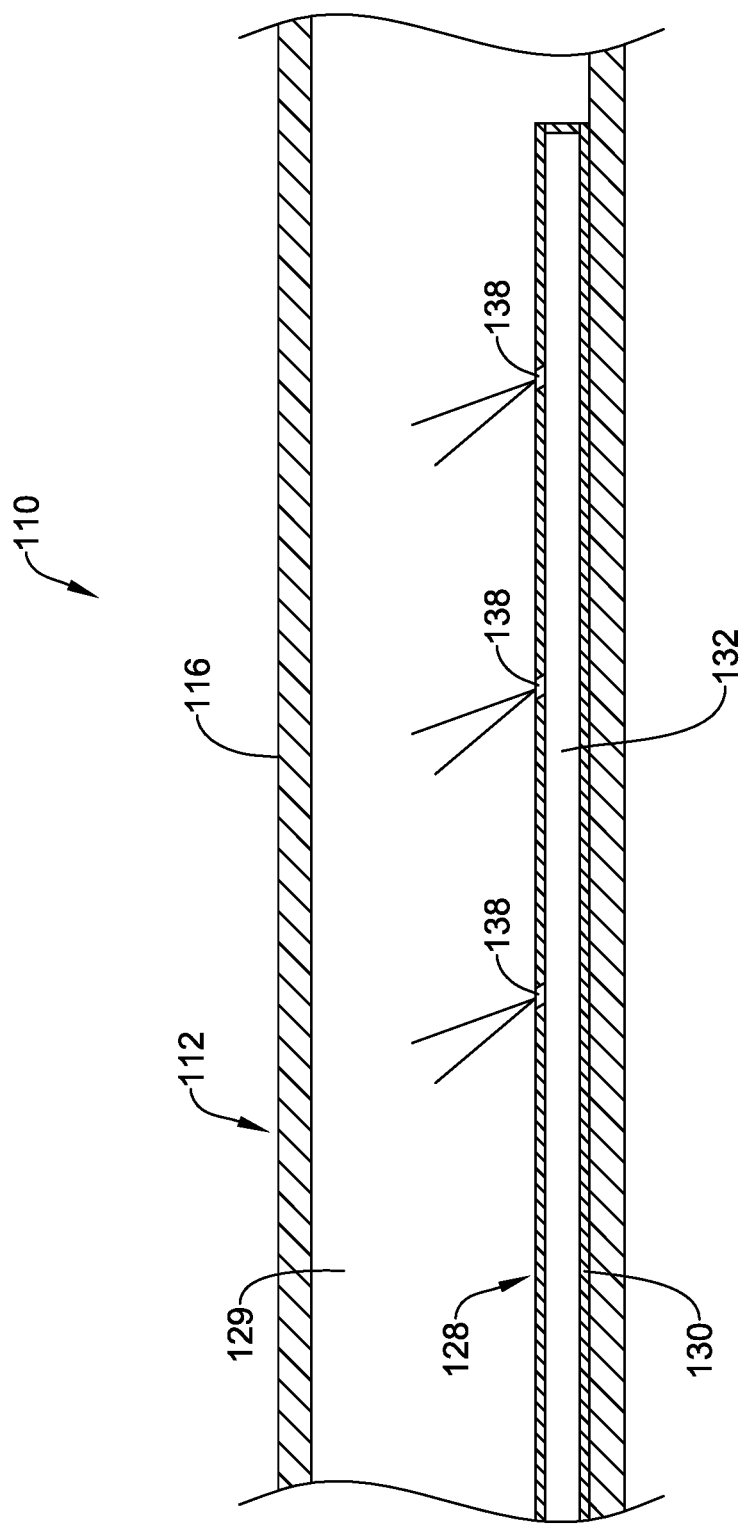
FIG. 4 is a cross-sectional side view of a portion of an example aspiration medical device.

FIGS. 3-4 illustrates an example aspiration member 128 (e.g., that may be similar in form and function to other aspiration members/assemblies disclosed herein) that may be used in an aspiration medical device 110. The aspiration medical device 110 (e.g., a portion of which is depicted in FIG. 4) may be similar in form and function to other aspiration medical devices disclosed herein. For example, the aspiration medical device 110 may include a catheter shaft 112 having a distal end region 116 and defining a lumen 129. The catheter shaft 112 may also include a first or inflow orifice (e.g., similar to the inflow orifice 22) and a second or outflow orifice (e.g., similar to the outflow orifice 24). For simplicity purposes, the inflow and outflow orifices are not shown in FIGS. 3-4.

The aspiration member 128 may be disposed in the lumen 129 of the catheter shaft 112. The aspiration member 128 may include a shaft 130 defining a lumen or fluid pathway 132. In at least some instances, the aspiration member 128 has a closed distal end. Because of this, fluid may be able to pass through the fluid pathway 132 but not exit the distal end the same way fluid may pass through the distal opening of a tube. In some instances, the aspiration member 128 may have an open distal end. Furthermore, the aspiration member 128 may differ from the aspiration assembly 28 (e.g., as shown in FIG. 2) in that the aspiration member 128 may lack a fluid jet 34.

A plurality of jet orifices 138 may be defined along the shaft 130. For example, the shaft 130 may include two, three, four, five, six, or more jet orifices 138. In some instances, some or all of the jet orifices 138 may be axially aligned along the shaft 130. In other instances, one or more of the jet orifices 138 may be circumferentially offset from one another about the shaft 130. A number of patterns are contemplated including a helical pattern, a regular pattern where no two jet orifices 138 are disposed at the same axial location, a regular pattern including two or more jet orifices 138 disposed at the same axial location, an irregular pattern (where some of the jet orifices 138 may or may not be disposed at the same axial location), etc. The jet orifices 138 may be formed using a suitable method such as electron discharge machining, etching, cutting (e.g., including laser cutting), or the like. In some instances, one or more of the jet orifices 138 have a substantially round shape. In other instances, one or more of the jet orifices 138 have a substantially non-round shape (e.g., oval, polygonal, irregular, etc.). In some instances, the jet orifices 138 may be beveled or otherwise include a beveled surface.

The jet orifices 138 may be designed to infuse fluid (e.g., a motive fluid, a liquid, a gas or air, steam, a fluid with particles disposed therein, or the like) through the jet orifices 138 and into the lumen 129 of the catheter shaft 112 in a generally proximal direction as depicted by lines projecting generally proximally from the jet orifices 138 in FIGS. 3-4. In some instances, the jet orifices 138 may be oriented at an angle relative to the longitudinal axis of the shaft 130. For example, the jet orifices 138 may be oriented at an acute angle relative to the longitudinal axis of the shaft 130 and/or oriented at an angle greater than zero degrees and less than ninety degrees relative to the longitudinal axis of the shaft 130. In other instances, the jet orifices 138 may be oriented at ninety degrees relative to the longitudinal axis of the shaft 130. The angle may or may not be the same for all the jet orifice 138. Infusion of motive fluid through the lumen 132 of the shaft 130 may result in fluid being jetted through the jet orifices 138 (e.g., generally in the proximal direction) and the generation of an aspiration force.

In at least some instances, the jet orifices 138 may be understood as being arranged in series. In other words, the jet orifices 138 may be arranged at various locations along the longitudinal axis of the shaft 130. This may position the jet orifices 138 at spaced apart axially locations within the catheter shaft 112. Accordingly, motive fluid leaves via the jet orifices forming a jetted motive fluid. This jetted motive fluid enters an entrainment material where the shear layer between the two causes turbulence, mixing, and transfer of momentum. Entrainment material may enter the inflow orifice (not shown, may be similar to the inflow orifice 22) and then may be urged proximally by momentum transfer. As the mixture of jetted motive fluid and entrainment material migrates proximally, the material may sequentially approach a number of jet orifices 138. Upon interaction with the jetted motive fluid from each individual jet orifice 138, the momentum in the entrainment material mixture may increase, and the thrombogenic material may more readily flow through the catheter shaft 112 for removal. The increase in momentum may allow for the catheter shaft 112 to be used without a second or outflow orifice (e.g., positioned proximally of the inflow orifice and that may be similar to the outflow orifice 24 as depicted in FIG. 2). Alternatively, some of the entrapped thrombogenic material may exit the catheter shaft 112 through a second orifice (not shown) positioned proximally of the inflow orifice, recirculate to the inflow orifice (e.g., one or more times), and then move through the lumen 129.

It can be appreciated that a relatively high volume of fluid, traveling at a high rate and pressure (e.g., on the order of about 290-580 miles per hour), may travel through the jet orifices 138. It may be desirable to reinforce the structural integrity of the jet orifices 138 and/or the catheter shaft 112. Disclosed herein are aspiration medical devices that include structural features configured to reinforce the structural integrity of the jet orifices 138 and/or the catheter shaft 112.

Figure 5:
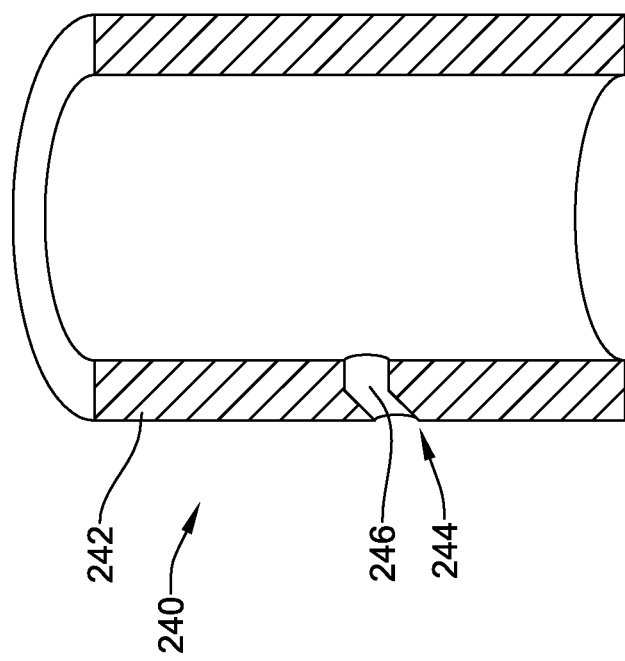
FIG. 5 is a cross-sectional view of an example collar.

FIG. 5 illustrates an example collar 240 that may be used with any of the aspiration medical devices disclosed herein. The collar 240 includes a body 242 having a jet support region 244. In general, the jet support region 244 is designed to support the jet orifices 138 in the aspiration member 128. A jet opening 246 may be formed in the collar 240, for example along the jet support region 244. The collar 240 may comprise a metal (e.g., titanium, aluminum, stainless steel and/or stainless steel alloys, etc.), polymer, or composite material that is capable of withstanding high volumes of fluid, traveling at a high rate and pressure, adjacent thereto. For example, the collar 240 may comprise a metal that can be positioned adjacent to a jet orifice and be capable of withstanding fluid passing through the jet orifice and contacting the collar 240. In some instances, the collar 240 may be a 3D printed collar 240 that can have a variety of different shapes and/or configurations.

Figure 6:
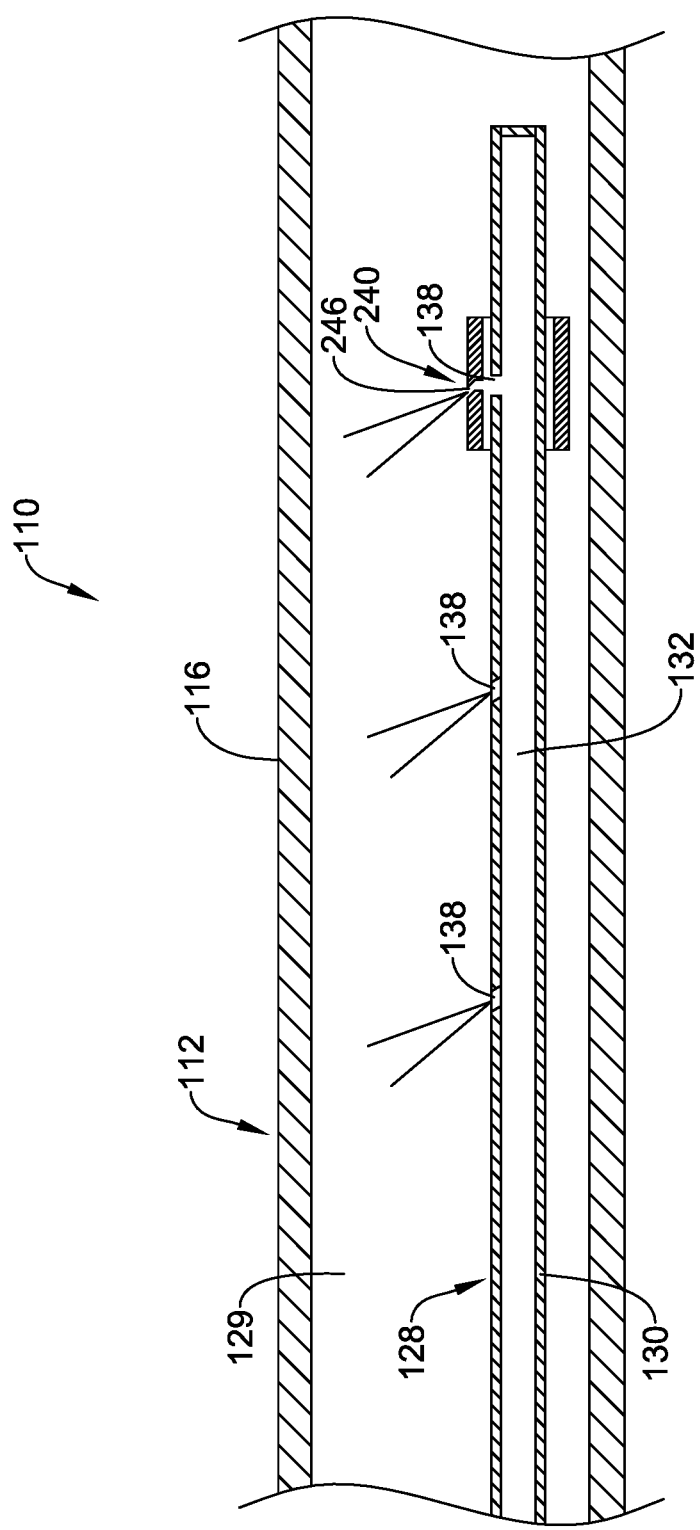
FIG. 6 is a cross-sectional side view of a portion of an example aspiration member including an example collar.

FIG. 6 illustrates the collar 240 disposed over/along the aspiration member 128. The collar 240 may be secured to the aspiration member 128 using a suitable securing technique such as adhesive bonding, thermal bonding, welding, etc. In this example, fluid passing through the jet orifices 138 may exit the aspiration member at a relatively high velocity. Due to the fluid traveling at a high velocity, it may be desirable to try to reduce the likelihood that the fluid could erode or otherwise impact the structural integrity of the jet orifices 138. As such, by disposing the collar 240 over/along the aspiration member 128, the collar 240 can enhance the structural integrity of the aspiration member 128, the jet orifices 138, and/or the aspiration medical device 110.

The jet opening 246 in the collar 240 may be aligned with one of the jet orifices 138. In some instances, the jet opening 246 is proximally angled and/or otherwise designed to direct fluid passing therethrough toward the proximal end of the aspiration medical device 110. This configuration may allow the jet orifice(s) 138 to be "square cut", oriented in a direction that is normal to a longitudinal axis of the aspiration member, and/or otherwise not be proximally angled. This may desirably impact the manufacturing the aspiration member 128 by simplifying the formation of the jet orifices 138. This may also help to reduce erosion or wear of the aspiration member 128 by virtue of the jet orifice 138 not having to be directed proximally as the proximally angled orientation of the jet opening 246 being sufficient to direct fluid proximally. Furthermore, because the collar 240 and the jet opening 246 therein may be formed using a process such as 3D printing (e.g., which allows for the formation of structure with a variety of configurations and designs including complex designs), the design of proximally angled cuts/openings (e.g., such as the jet opening 246) may be able to be controlled and manufactured more efficiently.

Figure 7:
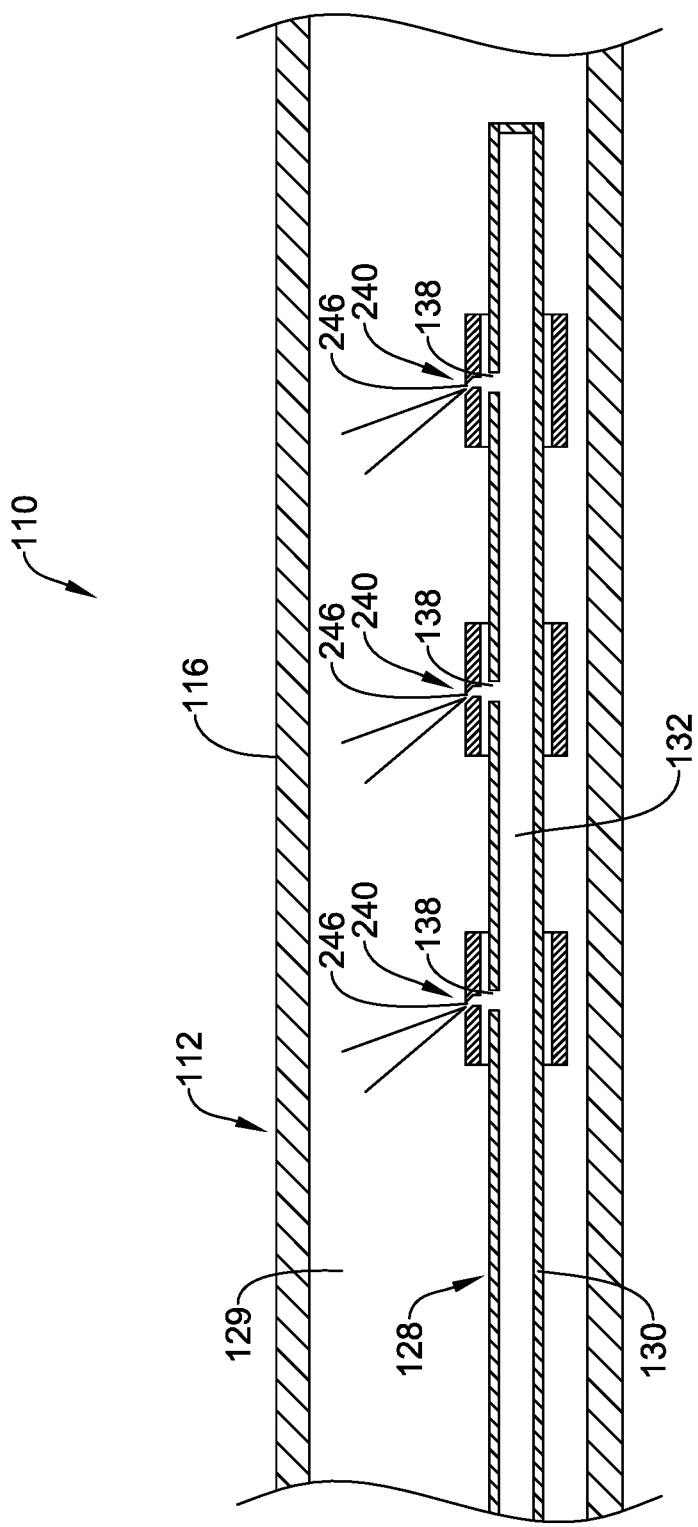
FIG. 7 is a cross-sectional side view of a portion of an example aspiration member including a plurality of example collars.

In FIG. 6, a single collar 340 is shown disposed over/along the aspiration member 128. The jet orifice 138 that is aligned with the jet opening 246 is square cut (e.g., not proximally angled) whereas the jet opening 246 is proximally angled. Fluid passing through the jet orifice 138 may pass through the proximally angled jet opening 246 and, thus, be directed proximally. In some instances, other jet orifices 138 along the aspiration member (e.g., which do not have a collar 340 disposed thereover in FIG. 6) may be proximally angled as shown in FIG. 6. However, this need not be the case. In some instances, the other jet orifices 138 may also be square cut. In such cases, the collar 340 may be extended to fit over multiple jet orifices 138 and include multiple jet openings 246 that each align with a jet orifice 138. Alternatively, a plurality of collars 240 may be disposed over/along the aspiration member 128 as shown in FIG. 7. This may include 2, 3, 4, 5, 6, or more collars 240 and/or all a suitable number of collars 240 to align with each/all of the jet orifices 138. In this example, each jet orifice 138 may be square cut and each collar 240 may include a proximally angled jet opening 246 that is proximally angled and aligned with respective jet orifices 138. Other configurations are contemplated.

Figure 8:
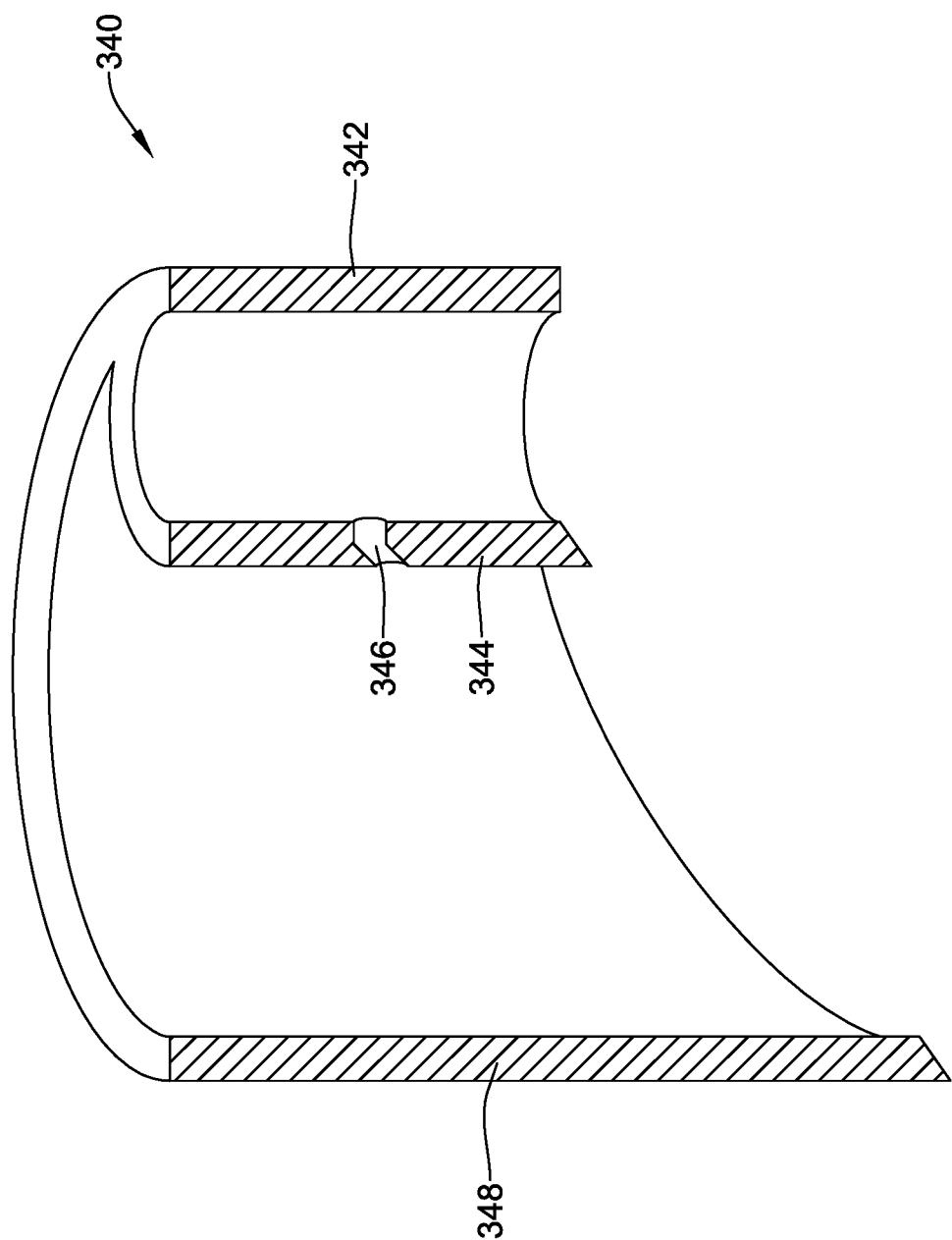
FIG. 8 is a cross-sectional view of an example collar.
Figure 9:
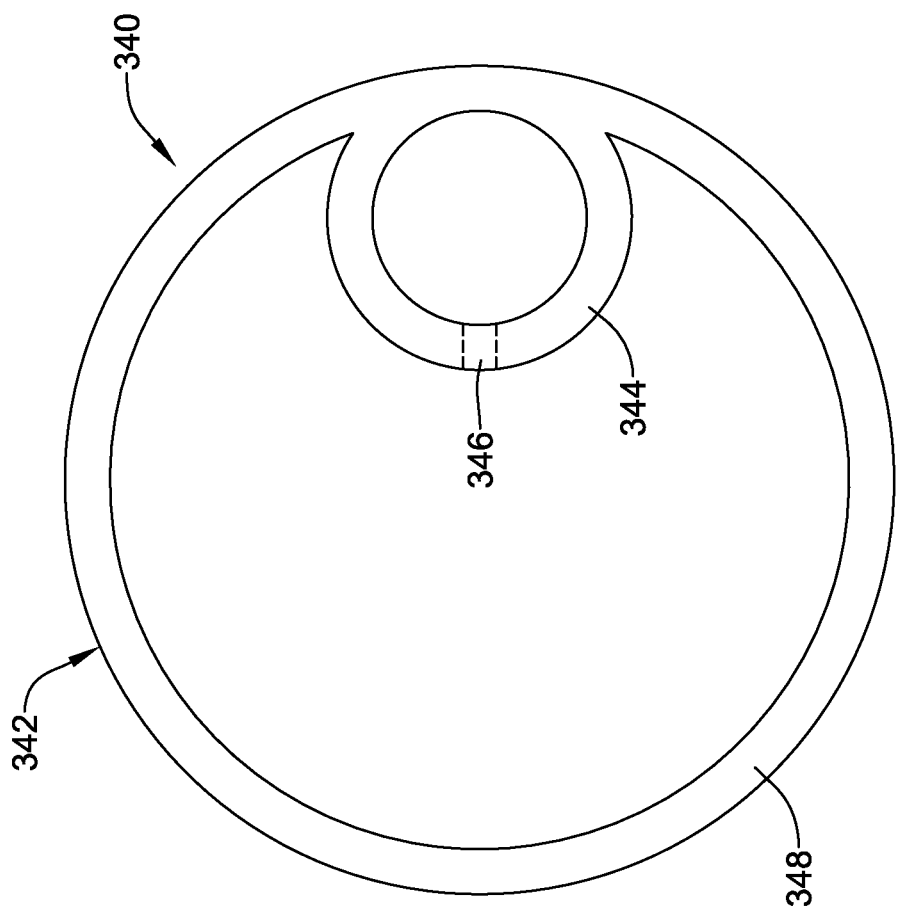
FIG. 9 is an end view of an example collar.

FIGS. 8-9 illustrate another example collar 340 that may be similar in form and function to other collars disclosed herein. The collar 340 includes a body 342 having a jet support region 344. A jet opening 346 may be formed in the collar 340, for example along the jet support region 344. In general, the jet support region 344 is designed to support the jet orifices 138 in the aspiration member 128. The jet support region 344 may have a cylindrical or tubular configuration that is configured to fit over/along the aspiration member 128. The collar 340 may also include a wall support region 348. In general, the wall support region 348 is designed to support the wall of the catheter shaft 112 (e.g., to reduce the likelihood that fluid passing through the jet orifices 138 could impact the integrity of the wall of the catheter shaft 112). The wall support region 348 may have a tubular and/or partially tubular/cylindrical configuration. In some instances, the shape of the wall support region 348 may be described as having an angled end, being skived, or have a flap or tailing end region.

Figure 10:
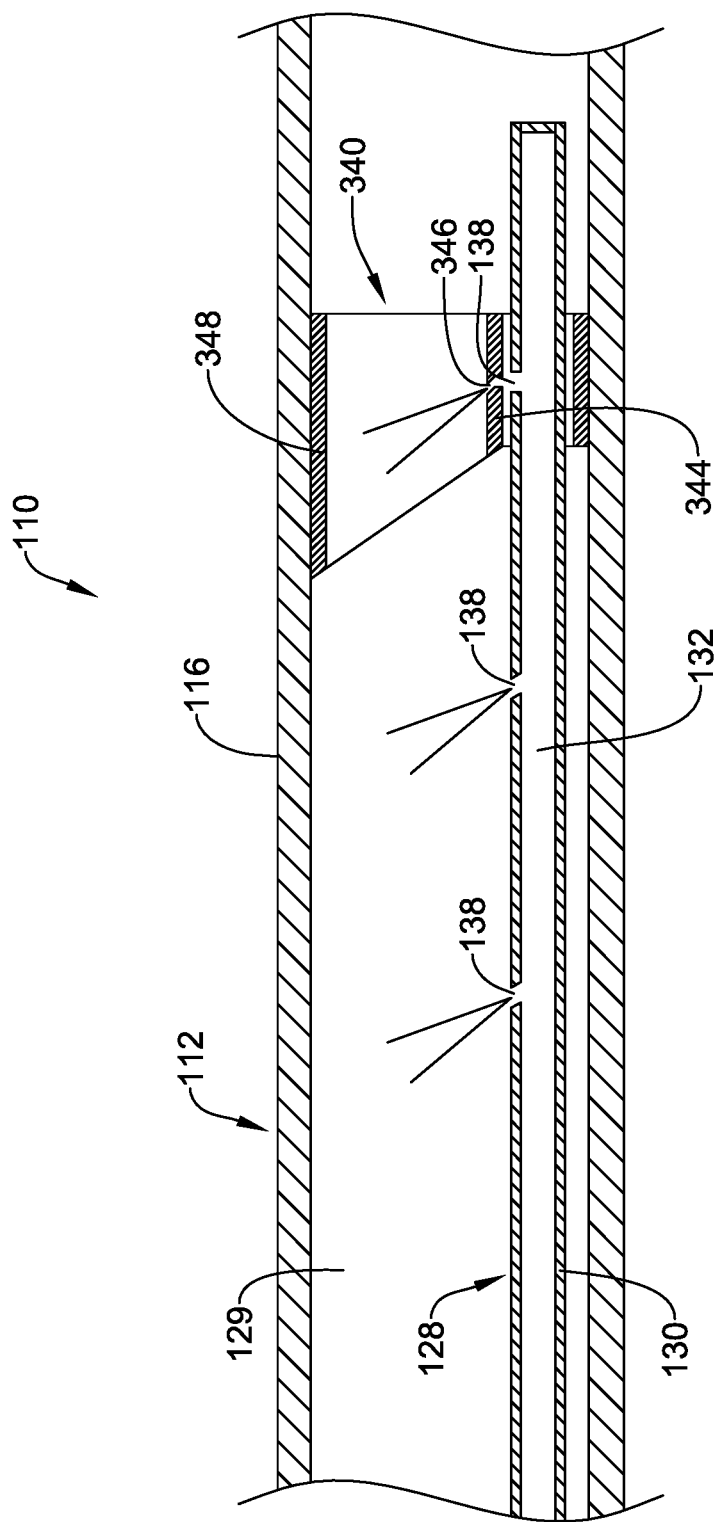
FIG. 10 is a cross-sectional side view of a portion of an example aspiration member including an example collar.
Figure 11:
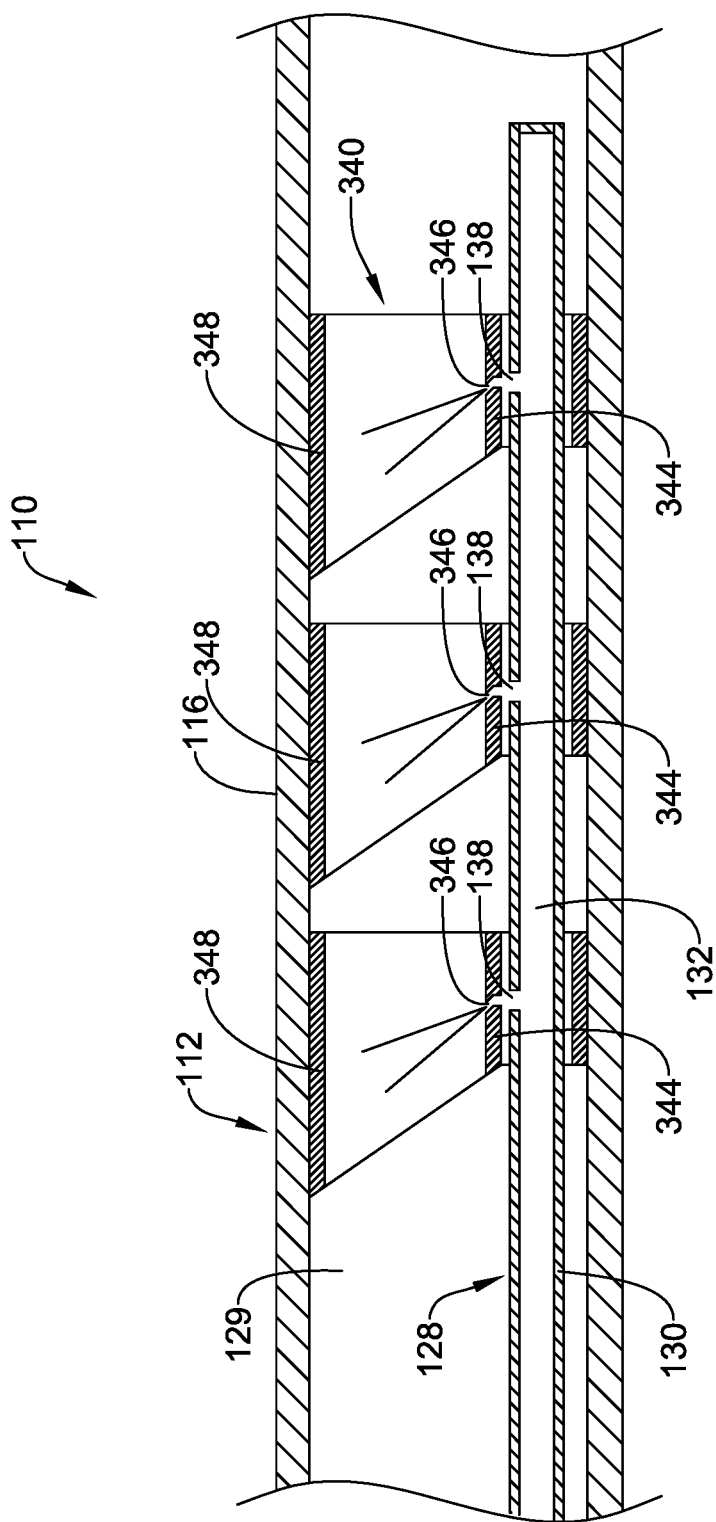
FIG. 11 is a cross-sectional side view of a portion of an example aspiration member including a plurality of example collars.

FIG. 10 illustrates the collar 340 disposed over/along the aspiration member 128. The collar 340 may be secured to the aspiration member 128 using a suitable securing technique such as adhesive bonding, thermal bonding, welding, etc. Just like the collar 240, the collar 340 may be arranged so that the jet opening 346 may be aligned with the jet orifice 138 of the aspiration member 128. Because the jet opening 346 may be proximally angled, the jet orifice 138 may be square cut. The wall support region 348 may be positioned along an interior wall of the catheter shaft 112, generally opposite the jet orifice 138. This may help to reduce the likelihood that fluid passing through the jet orifices 138 could impact the integrity of the wall of the catheter shaft 112. In some instances, a single collar 340 may be used with the aspiration member 128. Alternatively, a plurality of collars 340 may be disposed over/along the aspiration member 128 as shown in FIG. 11. This may include 2, 3, 4, 5, 6, or more collars 340 and/or all a suitable number of collars 340 to align with each/all of the jet orifices 138.

Figure 12:
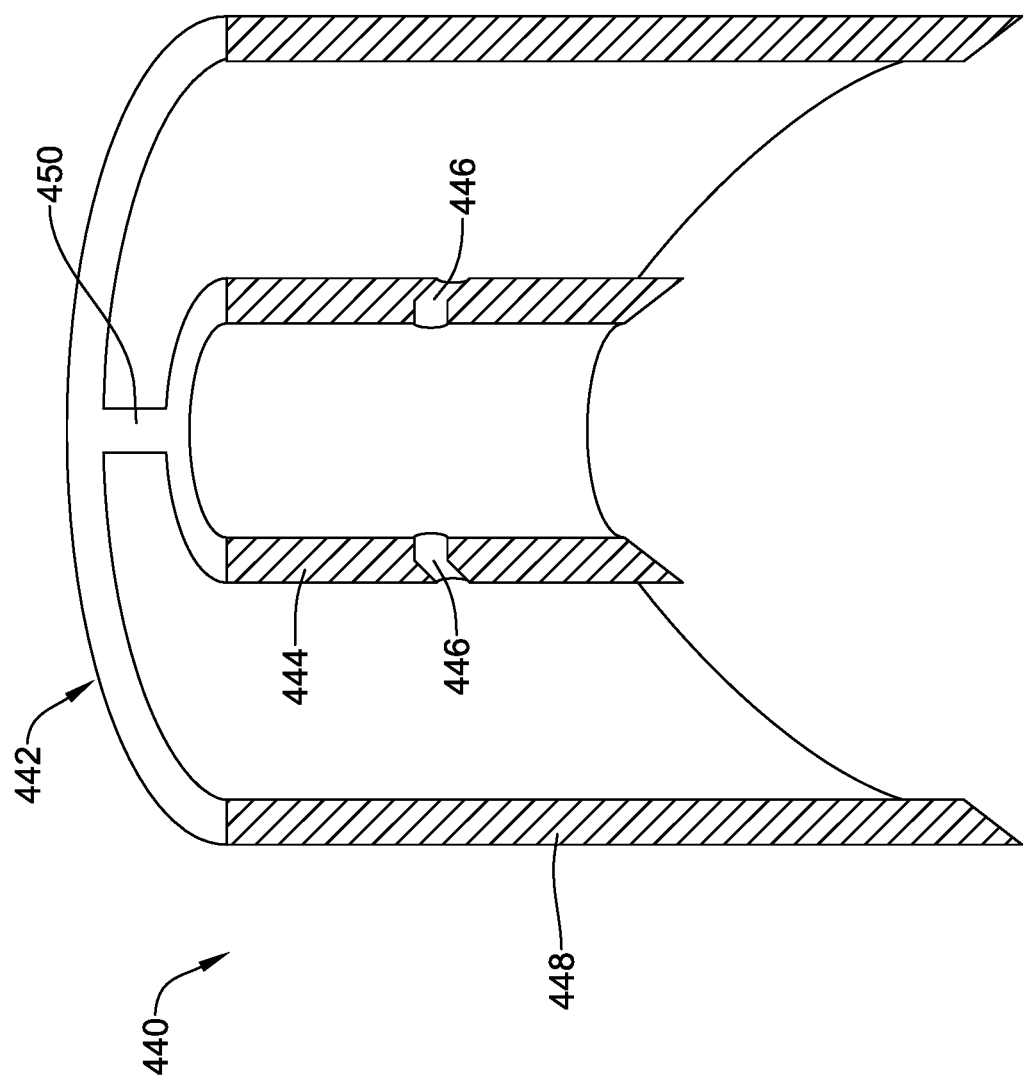
FIG. 12 is a cross-sectional view of an example collar.
Figure 13:
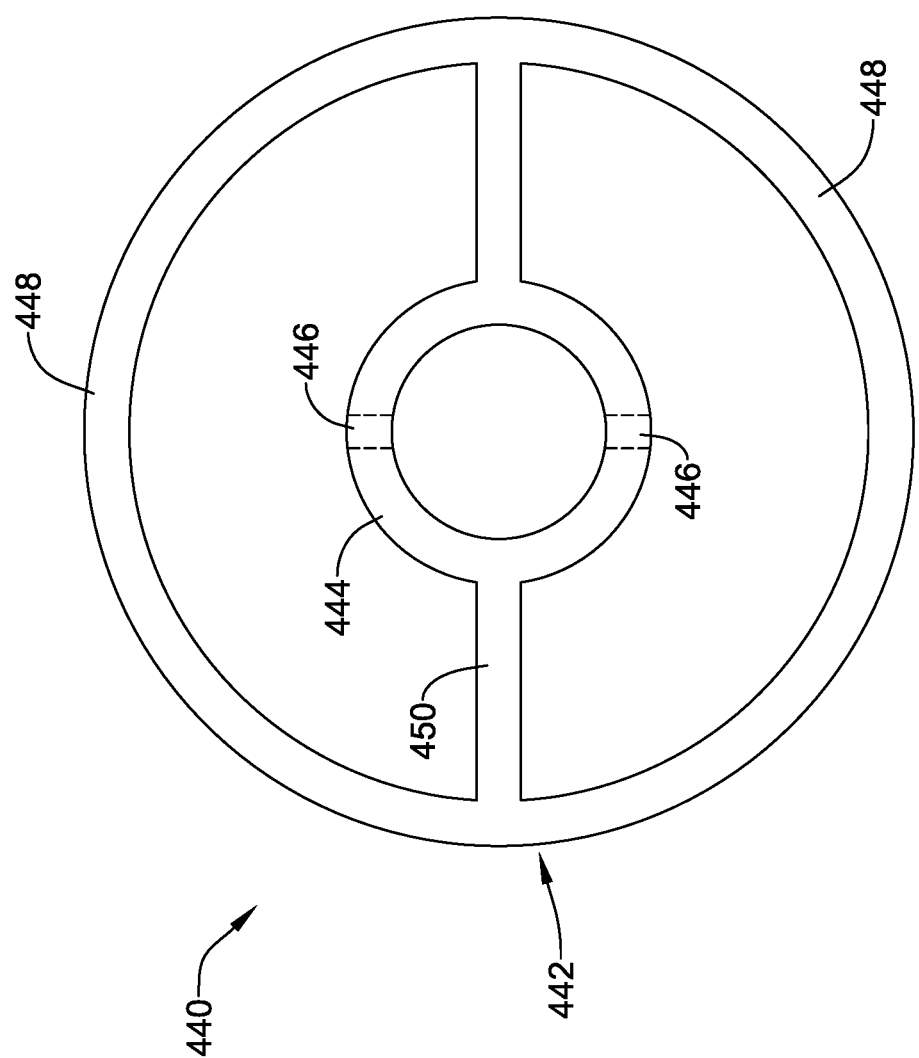
FIG. 13 is an end view of an example collar.
Figure 14:
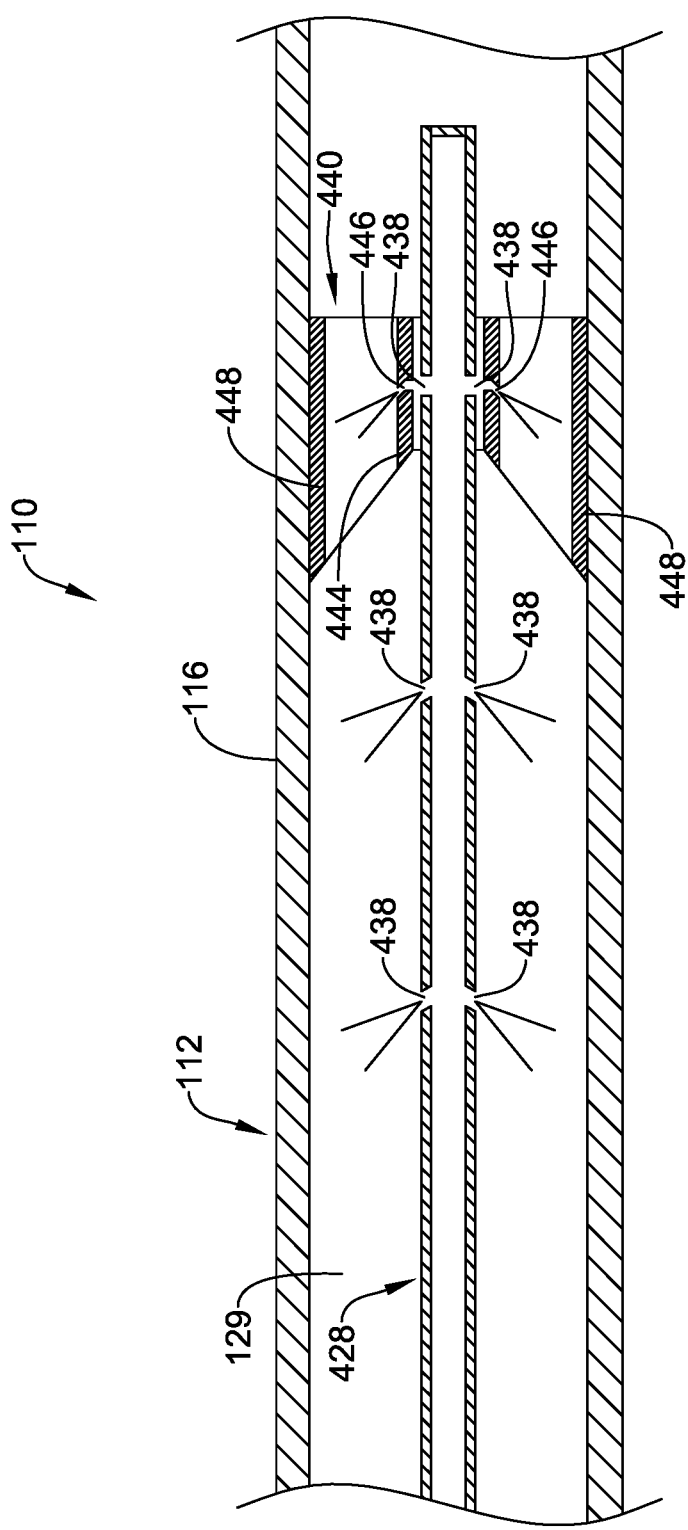
FIG. 14 is a cross-sectional side view of a portion of an example aspiration member including an example collar.
Figure 15:
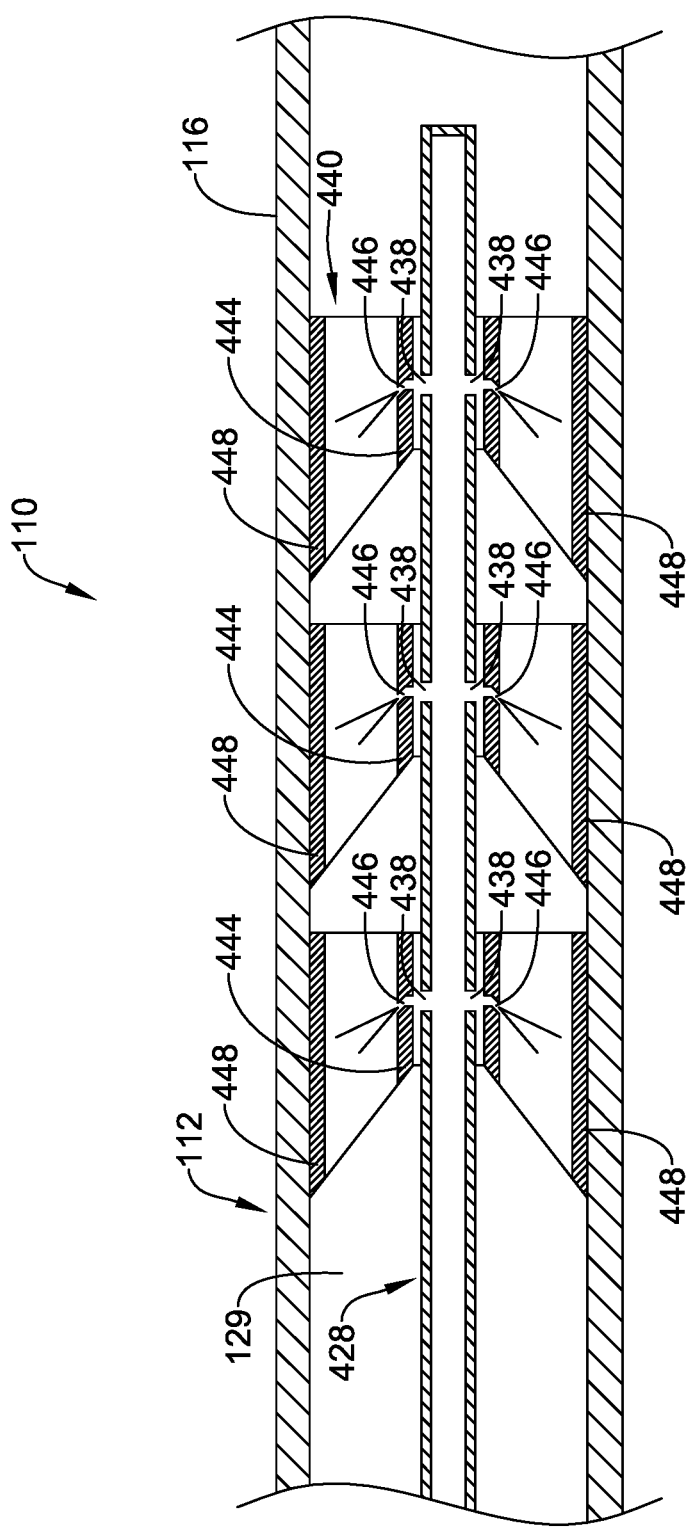
FIG. 15 is a cross-sectional side view of a portion of an example aspiration member including a plurality of example collars.

FIGS. 12-13 illustrate another example collar 440 that may be similar in form and function to other collars disclosed herein. The collar 440 includes a body 442 having a jet support region 444. In general, the jet support region 444 is designed to support the jet orifices 438 in the aspiration member 428 (e.g., the aspiration member 428 is shown in FIGS. 14-15). The jet support region 444 may have a cylindrical or tubular configuration that is configured to fit over/along the aspiration member 428. One or more jet openings 446 may be formed in the collar 440, for example along the jet support region 444. In this example, the jet support region 444 is substantially centered within the collar 440 and has a pair of opposing jet openings 446. Other configurations/arrangements are contemplated. The collar 440 may also include a wall support region 448 and a connecting region 450 extending between the jet support region 444 and the wall support region 448. In general, the wall support region 448 is designed to support the wall of the catheter shaft 112 (e.g., to reduce the likelihood that fluid passing through the jet orifices 438 could impact the integrity of the wall of the catheter shaft 112). The wall support region 448 may have a tubular and/or partially tubular/cylindrical configuration. In some instances, the shape of the wall support region 448 may be described as having an angled end, being skived, or have a flap or tailing end region.

FIG. 14 illustrates the collar 440 disposed over/along the aspiration member 428. The collar 440 may be secured to the aspiration member 428 using a suitable securing technique such as adhesive bonding, thermal bonding, welding, etc. In this example, the aspiration member 428 and the collar 440 coupled thereto may be substantially centered within the catheter shaft 112. Just like the collars 240, 340, the collar 440 may be arranged so that the jet opening 446 may be aligned with the jet orifice(s) 438 of the aspiration member 428. Because the jet openings 446 may be proximally angled, the jet orifice 438 may be square cut. The wall support region 448 may be positioned along an interior wall of the catheter shaft 112, generally opposite the jet orifices 438. This may help to reduce the likelihood that fluid passing through the jet orifices 438 could impact the integrity of the wall of the catheter shaft 112. In some instances, a single collar 440 may be used with the aspiration member 428. Alternatively, a plurality of collars 440 may be disposed over/along the aspiration member 128 as shown in FIG. 15. This may include 2, 3, 4, 5, 6, or more collars 440 and/or all a suitable number of collars 440 to align with each/all of the jet orifices.

The materials that can be used for the various components of the aspiration medical device 10 (and/or other aspiration medical devices disclosed herein) and the various components thereof may include those commonly associated with medical devices. For simplicity purposes, the following discussion refers to the catheter shaft 12 of the aspiration medical device 10. However, this is not intended to limit the devices and methods described herein, as the discussion may be applied to other catheter shaft and/or components of any of the aspiration medical devices disclosed herein.

The catheter shaft 12 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the catheter shaft 12 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the catheter shaft 12 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the catheter shaft 12 to achieve the same result.

In some embodiments, a degree of Magnetic Resonance Imaging (MRI) compatibility is imparted into the catheter shaft 12. For example, the catheter shaft 12, or portions thereof, may be made of a material that does not substantially distort the image and create substantial artifacts (e.g., gaps in the image). Certain ferromagnetic materials, for example, may not be suitable because they may create artifacts in an MRI image. The catheter shaft 12, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

U.S. Patent Application Pub. No. US 2017/0252057 is incorporated herein by reference.

U.S. Patent Application Pub. No. US 2019/0209745 is incorporated herein by reference.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. An aspiration medical device, comprising:
   a catheter shaft having a distal end region and defining an inflow orifice adjacent to the distal end region;
   an aspiration member disposed within the catheter shaft, the aspiration member having a plurality of fluid openings formed therein; and
   a wall support member disposed along an inner surface of the catheter shaft at a position opposite at least one of the fluid openings.

2. The aspiration medical device of claim 1, wherein at least one of the plurality of fluid openings is angled proximally.

3. The aspiration medical device of claim 1, wherein at least one of the plurality of fluid openings is oriented in a direction that is substantially normal to a longitudinal axis of the aspiration member.

4. The aspiration medical device of claim 1, wherein the plurality of fluid openings includes a first fluid opening and a second fluid opening disposed distally of the first fluid opening, wherein the first fluid opening is angled proximally, and wherein the second fluid opening is oriented in a direction that is substantially normal to a longitudinal axis of the aspiration member.

5. The aspiration medical device of claim 1, wherein the wall support member includes a fluid opening support region disposed adjacent to the aspiration member.

6. The aspiration medical device of claim 5, wherein the fluid opening support region is disposed adjacent to at least one of the plurality of fluid openings.

7. The aspiration medical device of claim 1, wherein the aspiration member has a closed distal end.

8. The aspiration medical device of claim 1, wherein the catheter shaft has an open distal end.

9. The aspiration medical device of claim 1, wherein the catheter shaft defines a guidewire lumen therein.

10. A medical device, comprising:
a catheter shaft having a distal end region and defining an inflow orifice adjacent to the distal end region;
a fluid infusion tube disposed within the catheter shaft, the fluid infusion tube having a plurality of axially-spaced openings formed therein; and
a support member disposed within the catheter shaft, the support member having a wall support region disposed along an inner surface of the catheter shaft at a position opposite at least one of the axially-spaced openings.

11. The medical device of claim 10, wherein at least one of the plurality of axially-spaced openings is angled proximally.

12. The medical device of claim 10, wherein at least one of the plurality of axially-spaced openings is oriented in a direction that is substantially normal to a longitudinal axis of the fluid infusion tube.

13. The medical device of claim 10, wherein the plurality of axially-spaced openings includes a first opening and a second opening disposed distally of the first opening, wherein the first opening is angled proximally, and wherein the second opening is oriented in a direction that is substantially normal to a longitudinal axis of the fluid infusion tube.

14. The medical device of claim 10, wherein the support member includes a fluid opening support region disposed adjacent to the fluid infusion tube.

15. The medical device of claim 14, wherein the fluid opening support region is disposed adjacent to at least one of the axially-spaced openings.

16. The medical device of claim 14, wherein the fluid infusion tube has a closed distal end.

17. The medical device of claim 14, wherein the catheter shaft defines a guidewire lumen therein.

18. An aspiration medical device, comprising:
a catheter shaft having a distal end region, the catheter shaft including an inflow orifice adjacent to the distal end region and an outflow orifice disposed proximally of the inflow orifice;
an aspiration member disposed within the catheter shaft, the aspiration member having a plurality of axially-spaced fluid jets formed therein including a first fluid jet and a second fluid jet disposed distally of the first fluid jet; and
a support member having a wall support region disposed adjacent an inner wall surface of the catheter shaft.

19. The aspiration medical device of claim 18, wherein the support member includes a collar region disposed along the aspiration member.

20. The aspiration medical device of claim 18, wherein the first fluid jet is angled proximally, and wherein the second fluid jet is oriented in a direction that is substantially normal to a longitudinal axis of the aspiration member.

* * * * *